United States Patent [19]
Belliotti et al.

[11] Patent Number: 5,945,421
[45] Date of Patent: Aug. 31, 1999

[54] DOPAMINE D4 RECEPTOR ANTAGONISTS

[75] Inventors: Thomas Richard Belliotti, Saline; Clifton John Blankley, Ann Arbor; Suzanne Ross Kesten, Ann Arbor; Lawrence David Wise, Ann Arbor; David Juergen Wustrow, Ann Arbor, all of Mich.

[73] Assignee: Warner-Lambert Company, Morris Plains, N.J.

[21] Appl. No.: 08/909,171

[22] Filed: Aug. 11, 1997

[51] Int. Cl.⁶ .................. A61K 31/495; A61K 31/47; C07D 401/06; C07D 403/06
[52] U.S. Cl. .................. 514/253; 514/314; 544/363; 546/175; 546/176
[58] Field of Search .................. 544/363; 514/253

[56] References Cited

U.S. PATENT DOCUMENTS

| | | | |
|---|---|---|---|
| 4,859,670 | 8/1989 | Kampe et al. | 514/252 |
| 5,206,366 | 4/1993 | Bowles | 544/368 |
| 5,240,919 | 8/1993 | Yous et al. | 514/210 |
| 5,300,507 | 4/1994 | Yous et al. | 514/253 |
| 5,322,843 | 6/1994 | Yous et al. | 514/233.8 |
| 5,322,849 | 6/1994 | Yous et al. | 514/321 |
| 5,326,775 | 7/1994 | Yous et al. | 514/375 |
| 5,386,034 | 1/1995 | Yous et al. | 548/169 |
| 5,436,348 | 7/1995 | Yous et al. | 548/221 |
| 5,607,946 | 3/1997 | Kulagowski et al. | 514/312 |

FOREIGN PATENT DOCUMENTS

| | | |
|---|---|---|
| 0296560A2 | 12/1988 | European Pat. Off. . |
| 0506539A1 | 9/1992 | European Pat. Off. . |
| 0579263A1 | 1/1994 | European Pat. Off. . |

OTHER PUBLICATIONS

Rao, V.A., et al., "Agents Acting on the Central Nervous System. XIII. 2,3,4,4a,5,6–Hexahydro–1(H)–pyrazino[1, 2–a]quinolines. A New Class of Hypotensive Agents," 1970, *J Med Chem*, 13:3, 516–522.

TenBrink et al., J.Med. Chem.39, pp. 2435–2437. 1996.

Kuroita et al., Chemical Abstracts, vol. 128, No. 61522 (Abstract for WO 9747601, Dec. 18, 1997). 1998.

Gazi et al., British Journal of Pharmacology, vol. 124, pp. 889–896. 1998.

Nityanand et al. Chemical Abstracts, vol. 78, No. 119132, 1973.

Kulagowski et al. Current Pharmaceutical Design,3, pp. 355–366, 1997.

Reynolds,Drugs, 51(1) pp. 7–11, 1996.

*Primary Examiner*—Emily Bernhardt
*Attorney, Agent, or Firm*—Todd M. Crissey

[57] ABSTRACT

This invention relates to compounds that are antagonists of dopamine D4 receptors, to methods of treating psychosis and schizophrenia using a compound that is an antagonist of dopamine D4 receptors, and to pharmaceutically acceptable compositions that contain a dopamine D4 receptor antagonist.

18 Claims, No Drawings

DOPAMINE D4 RECEPTOR ANTAGONISTS

FIELD OF THE INVENTION

This invention relates to compounds that are antagonists at dopamine D4 receptors, to methods of treating psychosis and schizophrenia using a compound that is an antagonist at dopamine D4 receptors, and to pharmaceutically acceptable compositions that contain a dopamine D4 receptor antagonist.

BACKGROUND OF THE INVENTION

Dopamine is a neurotransmitter that is found in the brains of animals, including humans, and is essential for proper nerve signal transmission. It is well-known that certain compounds block or inhibit the binding of dopamine to dopamine receptors. Such compounds are called dopamine receptor antagonists. It is also well-known that dopamine receptor antagonists are useful in the treatment of schizophrenia and psychosis.

Recently, it has been discovered that more than one type of dopamine receptor exists, and that dopamine receptor antagonists can preferentially inhibit one type of dopamine receptor over another. Two major families of dopamine receptors have been identified and named the D1 and D2 families. In the D2 family, three distinct receptor subtypes have been identified as D2, D3, and D4.

The distribution and concentration of the subtypes of receptors varies in different regions of the brain. D2 subtype receptors are located in both the limbic region of the brain, which is associated with cognition and emotional function, and in the striatum, which is associated with motor effects. D4 receptors are found in higher concentrations in the frontal cortex and limbic regions, which are associated with cognitive and emotional function.

Antipsychotic drugs that are D2 subtype receptor antagonists have been used to treat psychosis and schizophrenia, but have undesirable extrapyramidal side effects and produce tardive dyskinesia. In contrast, D4 receptor antagonists show a lack of extrapyramidal side effects and tardive dyskinesia. Moreover, it has been observed that the levels of dopamine D4 receptors are elevated in schizophrenics.

Thus, it would be useful to have compounds that are selective D4 antagonists for the treatment of psychosis and schizophrenia.

SUMMARY OF THE INVENTION

The present invention provides a compound of the Formula I

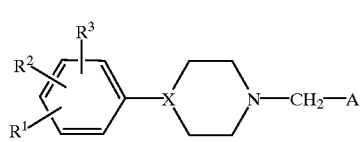

I wherein
A is 2, 3, 5, 6, 7, or 8 quinolinyl;
$R^1$, $R^2$, and $R^3$ are independently hydrogen, $C_1$–$C_6$ alkyl, halogen, $C_1$–$C_6$ alkoxy, $C_1$–$C_6$ thioalkoxy, hydroxymethyl, sulfonamido, carboxamido, —$CF_3$, —CN, —$NO_2$, —COH, or -alkyl-O-alkyl; and X is N or CH.

In a preferred embodiment of Formula I, X is N.
In a preferred embodiment of Formula I, X is CH.
In a preferred embodiment of Formula I, A is 2-quinolinyl.
In a preferred embodiment of Formula I, A is 3-quinolinyl.
In a preferred embodiment of Formula I, A is 6-quinolinyl.
In a preferred embodiment of Formula I, $R^1$ and $R^2$ are hydrogen, and $R^3$ is halogen, $C_1$–$C_6$ alkyl, or hydroxymethyl.
In a preferred embodiment of Formula I, $R^1$ is hydrogen, and $R^2$ and $R^3$ are independently halogen, hydroxymethyl, —$CF_3$, $C_1$–$C_6$ alkyl, $C_1$–$C_6$ alkoxy, —CN, —COH, or -alkyl-O-alkyl.
In a more preferred embodiment of Formula I, X is N, A is 2-quinolinyl, $R^1$ and R are hydrogen, and $R^3$ is halogen, $C_1$–$C_6$ alkyl, or hydroxymethyl.
In a more preferred embodiment of Formula I, X is N, A is 2-quinolinyl, $R^1$ is hydrogen, and $R^2$ and $R^3$ are independently halogen, hydroxymethyl, —$CF_3$, $C_1$–$C_6$ alkyl, $C_1$–$C_6$ alkoxy, —CN, —COH, or -alkyl-O-alkyl.

In a most preferred embodiment of Formula I, the compounds are:
2-(4-p-tolyl-piperazin-1-ylmethyl)-quinoline;
2-[4-(3-chloro-phenyl)piperazin-1-ylmethyl]-quinoline;
[2-chloro-4-(4-quinolin-2-ylmethyl-piperazin-1-yl)-phenyl]-methanol;
2-[4-(3,4-dimethyl-phenyl)-piperazin-1-ylmethyl]-quinoline;
2-[4-(4-fluoro-phenyl)-3,6-dihydro-2H-pyridin-1-ylmethyl]-quinoline;
2-[4-(3-chloro-4-methoxymethyl-phenyl)-piperazin-1-ylmethyl]quinoline;
[2-bromo-4-(4-quinolin-2-ylmethyl-piperazin-1-yl)-phenyl]-methanol;
2-[4-(3-chloro-4-methyl-phenyl)piperazin-1-ylmethyl]-quinoline;
2-[4-(3-bromo-phenyl)-piperazin-1-ylmethyl]-quinoline;
2-[4-(3-propyl-phenyl)-piperazin-1-ylmethyl]-quinoline;
2-[4-(2,3-dichloro-phenyl)piperazin-1-ylmethyl]-quinoline;
2-[4-(3,4-dichloro-phenyl)piperazin-1-ylmethyl]-quinoline;
[2-fluoro-4-(4-quinolin-2-ylmethyl-piperazin-1-yl)-phenyl]-methanol;
2-chloro-4-(4-quinolin-2-ylmethyl-piperazin-1-yl)-benzaldehyde;
2-chloro-4-(4-quinolin-2-ylmethyl-piperazin-1-yl)-benzonitrile;
2-[4-(4-methoxy-phenyl)piperazin-1-ylmethyl]-quinoline;
2-[4-(3,5-dichloro-phenyl)piperazin-1-ylmethyl]-quinoline;
2-[4-(4-chloro-3-trifluoromethyl-phenyl)-piperazin-1-ylmethyl]-quinoline;
2-(4-m-tolyl-piperazine-1-ylmethyl)-quinoline;
[4-(fluoro-4-(4-quinolin-3-ylmethyl-piperazin-1-yl)phenyl]-methanol;
[2-bromo-4-(4-quinolin-3-ylmethyl-piperazin-1-yl)phenyl]-methanol;
3-(4-phenyl-piperazin-1-ylmethyl)-quinoline;
3-(4-p-tolyl-piperazin-1-ylmethyl)-quinoline;
6-(4-phenyl-piperazin-1-ylmethyl)-quinoline; or
3-[4-(2-fluoro-phenyl)piperazin-1-ylmethyl]-quinoline.

Also provided by the present invention is a method of treating psychosis, the method comprising administering to a patient suffering therefrom a therapeutically effective amount of a compound of Formula I.

Also provided by the present invention is a method of treating schizophrenia, the method comprising administering to a patient suffering therefrom a therapeutically effective amount of a compound of Formula I.

Also provided by the present invention is a pharmaceutically acceptable composition that comprises a compound of Formula I.

DETAILED DESCRIPTION OF THE INVENTION

The present invention provides a compound of the Formula I

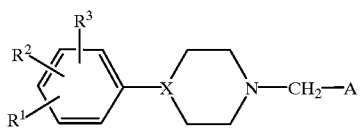

wherein
A is 2, 3, 5, 6, 7, or 8 quinolinyl;
$R^1$, $R^2$, and $R^3$ are independently hydrogen, $C_1$–$C_6$ alkyl, halogen, $C_1$–$C_6$ alkoxy, $C_1$–$C_6$ thioalkoxy, hydroxymethyl, sulfonamido, carboxamido, —$CF_3$, —CN, —$NO_2$, —COH, or -alkyl-O-alkyl; and
X is N or CH.

The term "alkyl" means a straight or branched chain hydrocarbon. Representative examples of alkyl groups are methyl, ethyl, propyl, isopropyl, isobutyl, butyl, tert-butyl, sec-butyl, pentyl, and hexyl.

The term "alkoxy" means an alkyl group attached to an oxygen atom. Representative examples of alkoxy groups include methoxy, ethoxy, tert-butoxy, propoxy, and isobutoxy.

The term "halogen" includes chlorine, fluorine, bromine, and iodine.

The symbol "—" means a bond.

The atoms in the quinoline group are numbered as shown below:

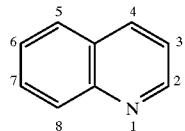

The term "patient" includes humans.

A "therapeutically effective amount" is an amount of a compound of the present invention that when administered to a patient ameliorates a symptom of psychosis or schizophrenia. A therapeutically effective amount of a compound of the present invention can be easily determined by one skilled in the art by administering a quantity of a compound to a patient and observing the result. In addition, those skilled in the art are familiar with identifying patients having psychosis and schizophrenia and are readily able to identify patients who suffer from psychosis and schizophrenia.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgement, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention.

The term "salts" refers to the relatively nontoxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactiobionate and laurylsulphonate salts, and the like. These may include cations based on the alkali and alkaline earth metals such as sodium, lithium, potassium, calcium, magnesium, and the like, as well as nontoxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, S. M. Berge, et al., "Pharmaceutical Salts," *J. Pharm. Sci.*, 66:1–19 (1977) which is incorporated herein by reference.)

Examples of pharmaceutically acceptable, nontoxic esters of the compounds of this invention include $C_1$ to $C_6$ alkyl esters wherein the alkyl group is a straight or branched chain. Acceptable esters also include $C_5$ to $C_7$ cycloalkyl esters as well as arylalkyl esters such as, but not limited to benzyl. $C_1$ to $C_4$ alkyl esters are preferred. Esters of the compounds of the present invention may be prepared according to conventional methods.

The term "prodrug" refers to compounds that are rapidly transformed in vivo to yield the parent compound of the above formulas, for example, by hydrolysis in blood. A thorough discussion is provided in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are incorporated herein by reference.

The compounds of the present invention can be administered to a patient alone or as part of a composition that contains other components such as excipients, diluents, and carriers, all of which are well-known in the art. The compositions can be administered to humans and animals either orally, rectally, parenterally (intravenous, by intramuscularly or subcutaneously), intracisternally, intravaginally, intraperitoneally, intravesically, locally (powders, ointments or drops), or as a buccal or nasal spray.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose and acacia; (c) humectants, as for example, glycerol; (d) disintegrating agents, as for example, agar-agar, calcium carbonate, potato or tapioca starch, alginic acid, certain complex silicates and sodium carbonate; (e) solution retarders, as for example paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well-known in the art. They may contain opacifying agents and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable nonirritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is sufficient. The specific dosage used, however, can vary. For example, the dosage can depended on a numbers of factors including the requirements of the patient, the severity of the condition being treated, and the pharmacological activity of the compound being used. The determination of optimum dosages for a particular patient is well-known to those skilled in the art.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The compounds of the present invention can exist in different stereoisometric forms by virtue of the presence of asymmetric centers in the compounds. It is contemplated that all stereoisometric forms of the compounds as well as mixtures thereof, including racemic mixtures, form part of this invention.

EXAMPLES

The compounds of the present invention are made in one of two ways: either alkylation of chloromethyl quinolines with the corresponding aryl piperazine or by reductive amination of quinoline aldehydes.

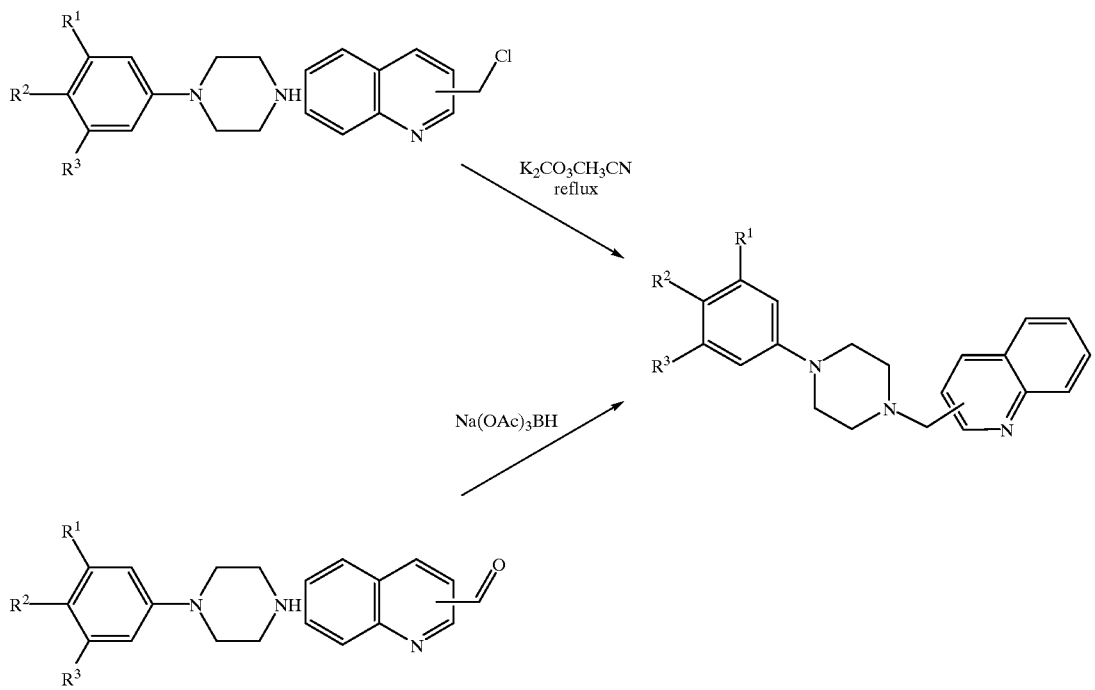

The aryl piperazines are commercially available or are prepared as shown below:

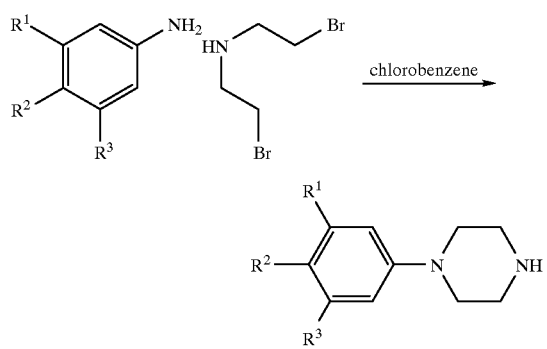

The chloromethyl quinolines and quinolinyl carboxaldehydes are either commercially available or can be obtained by methods obvious to one skilled in the art from the corresponding quinoline methanols which can be prepared according to Kaslow, et al., *J. Org. Chem.*, 18:55 (1953), which is hereby incorporated by reference.

PREPARATIVE EXAMPLES

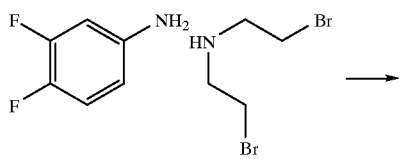

-continued

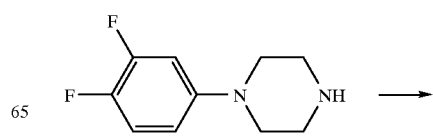

Preparation of 1-(3,4-difluoro-phenyl)-piperazine dihydrochloride

A mixture of 3,4-difluoroaniline (3.6 g) and bis(2-bromoethyl)amine hydrochloride (5.0 g) in 50 mL of chlorobenzene is warmed to reflux under argon for 48 hours. The mixture is cooled to room temperature, diluted with 100 mL of diethyl ether, and extracted with three 150 mL portions of 1N HCl. The aqueous extracts are backwashed with three 50 mL portions of ether, which are discarded. The combined aqueous fractions are basified to pH 11 with 12N NaOH. The resulting mixture is extracted with three 50 mL portions of methylene chloride, and the combined organic extracts are dried over sodium sulfate. The solvent is removed under reduced pressure, and the resulting residue is taken up in 50 mL of diethyl ether and filtered through Celite. The resulting solution is treated with a 1 M ethereal HCl solution (56 mL), and the resulting precipitate is collected and dried under vacuum to give 5.1 g of the title compound, mp 100–104° C. (decomposes).

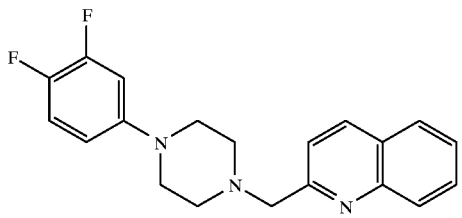

Preparation of 2-[4-(3,4-difluoro-phenyl)-piperazin-1-ylmethyl]-quinoline

A mixture of 2-chloromethylquinoline hydrochloride (1.0 g, 6.4 mmol), 1-(3,4-difluoro-phenyl)-piperazine dihydrochloride and potassium carbonate (8.8 g) in acetonitrile (50 mL) is warmed to reflux under argon for 18 hours. The mixture is cooled to room temperature, and the solvent is removed under reduced pressure. The solid remaining is partitioned between 50 mL of methylene chloride and 50 mL of water. The organic layers are separated and washed with brine and dried over $Na_2SO_4$. Evaporation of the solution gives a dark solid which is recrystallized twice from hexane to give 0.47 g (22% yield) of the title compound, mp 119–121° C.

In a similar way, the following compounds were prepared:
2-(4-p-tolyl-piperazin-1-ylmethyl)-quinoline, mp 64–68° C.;
2-[4-(3-chloro-phenyl)-piperazin-1-ylmethyl]-quinoline, mp 101–103° C.;
2-[4-(3,4-dimethyl-phenyl)-piperazin-1-ylmethyl]-quinoline, mp 80–82° C.;
2-[4-(4-fluoro-phenyl)-3,6-dihydro-2H-pyridin-1-ylmethyl]-quinoline, mp 83–84° C.;
2-[4-(3-chloro-4-methoxymethyl-phenyl)-piperazin-1-ylmethyl]-quinoline oil;
[2-chloro-4-(4-quinolin-2-ylmethyl-piperazin-1-yl)-phenyl]-methanol, mp 151–152° C.;
[2-bromo-4-(4-quinolin-2-ylmethyl-piperazin-1-yl)-phenyl]-methanol, mp 149–150° C.;
2-[4-(3-chloro-4-methyl-phenyl)-piperazin-1-ylmethyl] quinoline, mp 82–84° C.;
2-[4-(3-bromo-phenyl)-piperazin-1-ylmethyl]-quinoline, mp 95–96° C.;
2-[4-(3-propyl-phenyl)-piperazin-1-ylmethyl]-quinoline, mp 83–85° C.;
2-[4-(2,3-dichloro-phenyl)-piperazin-1-ylmethyl]-quinoline, mp 156–158° C.;
2-[4-(3,4-dichloro-phenyl)-piperazin-1-ylmethyl]-quinoline, mp 140–142° C.;
[2-fluoro-4-(4-quinolin-2-ylmethyl-piperazin-1-yl)-phenyl]-methanol, mp 130–131° C.;
2-chloro-4-(4-quinolin-2-ylmethyl-piperazin-1-yl)-benzaldehyde, mp 124–125° C.;
Chloro-4-(4-quinolin-2-ylmethyl-piperazin-1-yl)-benzonitrile, mp 158–160° C.;
2-[4-(4-methoxy-phenyl)-piperazin-1-ylmethyl]-quinoline, mp 88–90° C.;
2-[4-(3,5-dichloro-phenyl)-piperazin-1-ylmethyl]-quinoline oil;
2-[4-(4-chloro-3-trifluoromethyl-phenyl)-piperazin-1-ylmethyl]-quinoline oil;
2-(4-m-tolyl-piperazin-1-ylmethyl)-quinoline, mp 61–64° C.;
[4-(4-quinolin-2-ylmethyl-piperazin-1-yl)-phenyl]-methanol oil; and
2-[4-(3,4-difluoro-phenyl)-piperazinyl-1-ylmethyl]-quinoline, mp 119–120° C.;

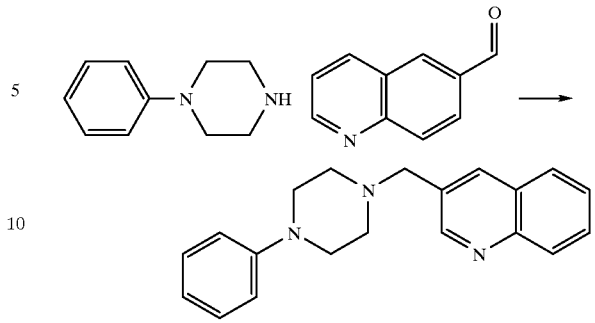

3-(4-Phenyl-piperazin-1-ylmethyl)-quinoline

A mixture of 3-quinoline carboxaldehyde (1 g, 6.36 mmol) and 1-phenylpiperazine (6.68 mmol), and sodium triacetoxyborohydride (2 g, 9.6 mmol) and 20 mL of dichloroethane, is stirred at room temperature for 18 hours. The resulting mixture is partitioned between chloroform and aqueous sodium bicarbonate, the organic layer is dried over sodium sulfate, and the solvents were removed under reduced pressure. The residue was recrystallized from ethyl acetate to give 1.2 g of the title compound as a white solid, mp 145–147° C.

In a similar way, the following compounds were prepared:
3-(4-p-tolyl-piperazinyl-1-ylmethyl)-quinoline, mp 126–127° C.;
3-[4-(2-fluorophenyl)-piperazin-1-ylmethyl]-quinoline, mp 136–137° C.; and
6-(4-phenyl-piperazin-1-ylmethyl)-quinoline, mp 95–99° C.

Cell Lines Expressing Dopamine Receptor Isoforms

A cell line expressing human dopamine D2 (Long form) receptors was purchased from Oregon Health Sciences University, Portland, Oreg. The D2 receptor cDNA was subcloned into an expression vector, pRc/CMV. The plasmids were transfected by electroporation into CHO K1 cells. A single stable transfectant, resistant to the antibiotic G418, was isolated and selected for use in the binding studies. For D4 binding, CHO K1 cells stably transfected to express the human recombinant dopamine D4.2 receptor subtype, as described by Shih, et al., "The expression and functional characterization of human dopamine D4.2 receptor in CHO K1 cells," *Soc. Neurosci.*, 21(Part 1):621 (1995).

Cell Culture and Preparation of Cell Membranes

CHO K1 cells expressing either human D2 and D4.2 receptors were grown in 162 $cm^2$ culture flasks in F12 medium (Gibco Laboratories, Grand Island, N.Y.) supplemented with 10% fetal bovine serum (FBS, Hyclone, Logan, Utah) in an atmosphere of 5% $CO_2$/95% air at 37° C. Cells were grown until confluent, after which growth medium was removed and replaced with 0.02% ethylene diamine tetracetate (EDTA) in a phosphate-buffered saline solution (Sigma Chemical Co., St. Louis, Mo.) and scraped from the flasks. The cells were centrifuged at about 1000×g for 10 minutes at 40° C. and then resuspended in TEM buffer (25 mM Tris-HCL, pH 7.4, 5 mM EDTA, and 6 mM $MgCl_2$) for D2 or the D4.2 buffer (50 mM Tris-HCl, pH 7.4, 5 mM EDTA, 1.5 mM $CaCl_2$, 5 mM KCl, and 120 mM NaCl) and homogenized. The membranes were pelleted by centrifugation at 20,000×g at 40° C. for 20 minutes. Then the pellets were resuspended in appropriate buffer at 1 mL/flask and stored at −70° C. until used in the receptor binding assay.

Receptor Binding Assays: D2, D4.2 Dopamine Receptors

A cell membrane preparation (400 μL) was incubated in triplicate with 50 μL [$^3$H]spiperone (0.2 nM for D2, 0.2 nM for D4.2), 50 μL buffer, or competing drugs where appropriate to give a final volume of 0.5 mL. After 60 minutes incubation at 25° C., the incubations were terminated by rapid filtration through Whatmann GF/B glass fibre filters (soaked for 1 hour in 0.5% polyethylenimine) on a -cell harvester, with three washes of 1 mL ice-cold buffer. Individual filter disks containing the bound ligand were placed in counting vials with 4 mL of scintillation fluid (Ready Gel, Beckman Instrument Inc., Fullerton, Calif.) and then counted in a Beckman LS-6800 liquid scintillation counter at an efficiency of 45%. Nonspecific binding was defined in presence of 1 mM of haloperidol.

Data Calculation

Saturation and competition binding data were analyzed using an iterative nonlinear least-square curve-fitting Ligand program. In competition experiments, apparent $K_i$ values were calculated from $IC_{50}$ values by method of Cheng and Prusoff, "Relationship between the inhibition constant ($K_i$) and the concentration of inhibitor which causes 50% inhibition ($IC_{50}$) of an enzymatic reaction," *Biochem. Pharmacol.*, 22:3099–3108 (1973). Experimental compounds were made up as stock solutions in dimethyl sulfoxide (DMSO). The final concentration of 0.1% DMSO used in the incubation mixture had no effect on the specific binding. Each observation was carried out in triplicate. To allow these calculations, $K_d$ values were measured for the interaction of various ligands with the receptor. These were: [$^3$H]spiperone binding, human D2, 0.116+0.01 and human D4.2, 0.093+0.005 nM (n=3). The test results are presented below in Table 1.

TABLE 1

| Compound Name | D4 $K_i$ (nm) | D2 $K_i$ (nm) |
| --- | --- | --- |
| 2-(4-p-Tolyl-piperazin-1-ylmethyl)-quinoline | 1.55 | 2847 |
| 2-[4-(3-Chloro-phenyl)-piperazin-1-ylmethyl]-quinoline | 2.72 | >5882 |
| [2-Chloro-4-(4-quinolin-2-ylmethyl-piperazin-1-yl)-phenyl]-methanol | 8.27 | >10000 |
| 2-[4-(3,4-Dimethyl-phenyl)-piperazin-1-ylmethyl]-quinoline | 13 | >5882 |
| 2-[4-(4-Fluoro-phenyl)-3,6-dihydro-2H-pyridin-1-ylmethyl]-quinoline | 14.4 | 254 |
| 2-[4-(3-Chloro-4-methoxymethyl-phenyl)-piperazin-1-ylmethyl]-quinoline | 31.5 | >5882 |
| [2-Bromo-4-(4-quinolin-2-ylmethyl-piperazin-1-yl)-phenyl]-methanol | 36 | >5882 |
| 2-[4-(3-Chloro-4-methyl-phenyl)-piperazin-1-ylmethyl]-quinoline | 36 | >5882 |
| 2-[4-(3-Bromo-phenyl)-piperazin-1-ylmethyl]-quinoline | 46 | |
| 2-[4-(3-Propyl-phenyl)-piperazin-1-ylmethyl]-quinoline | 57 | 5811 |
| 2-[4-(2,3-Dichloro-phenyl)-piperazin-1-ylmethyl]-quinoline | 59.5 | |
| 2-[4-(3,4-Dichloro-phenyl)-piperazin-1-ylmethyl]-quinoline | 61 | >5882 |
| [2-Fluoro-4-(4-quinolin-2-ylmethyl-piperazin-1-yl)-phenyl]-methanol | 87 | |
| 2-Chloro-4-(4-quinolin-2-ylmethyl-piperazin-1-yl)-benzaldehyde | 87 | |
| 2-Chloro-4-(4-quinolin-2-ylmethyl-piperazin-1-yl)-benonitrile | 101 | |
| 2-[4-(4-Methoxy-phenyl)-piperazin-1-ylmethyl]-quinoline | 101 | |
| 2-[4-(3,5-Dichloro-phenyl)-piperazin-1-ylmethyl]-quinoline | 121 | |
| 2-[4-(4-Chloro-3-trifluoromethyl-phenyl)-piperazin-1-ylmethyl]-quinoline | 122 | |
| 2-(4-m-Tolyl-piperazin-1-ylmethyl)-quinoline | 127 | |

TABLE 1-continued

| Compound Name | D4 $K_i$ (nm) | D2 $K_i$ (nm) |
| --- | --- | --- |
| [4-(4-Quinolin-2-ylmethyl-piperazin-1-yl)-phenyl]-methanol | 139 | >5882 |
| [2-Fluoro-4-(4-quinolin-3-ylmethyl-piperazin-1-yl)-phenyl]-methanol | 8.8 | >5882 |
| [2-Bromo-4-(4-quinolin-3-ylmethyl-piperazin-1-yl)-phenyl]-methanol | 13.5 | >5882 |
| 3-(4-Phenyl-piperazin-1-ylmethyl)-quinoline | 16 | 1789 |
| 3-(4-p-Tolyl-piperazin-1-ylmethyl)-quinoline | 21 | 2162 |
| 6-(4-Phenyl-piperazin-1-ylmethyl)-quinoline | 26 | 1383 |
| 3-[4-(2-Fluoro-phenyl)-piperazin-1-ylmethyl]-quinoline | 29 | 512 |

We claim:

1. A method of treating psychoses, the method comprising administering to a patient suffering therefrom a therapeutically effective amount of a compound of Formula I

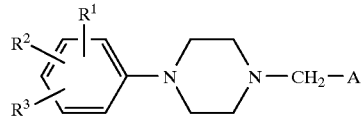

I wherein
A is 2, 3, 5, 6, 7, or 8 quinolinyl; and
$R^1$, $R^2$, and $R^3$ are independently hydrogen, $C_1$–$C_6$ alkyl, halogen, $C_1$–$C_6$ alkoxy, $C_1$–$C_6$ thioalkoxy, hydroxymethyl, sulfonamido, carboxamido, —$CF_3$, —CN, —$NO_2$ —C(═O)H, or —$CH_2OCH_3$, or a pharmaceutically acceptable salt thereof.

2. A method of treating schizophrenia, the method comprising administering to a patient suffering therefrom a therapeutically effective amount of a compound of Formula I

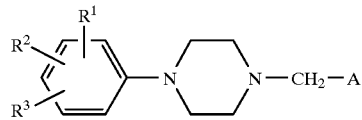

I wherein
A is 2, 3, 5, 6, 7, or 8 quinolinyl; and
$R^1$, $R^2$, and $R^3$ are independently hydrogen, $C_1$–$C_6$ alkyl, halogen, $C_1$–$C_6$ alkoxy, $C_1$–$C_6$ thioalkoxy, hydroxymethyl, sulfonamido, carboxamido, —$CF_3$, —CN, —$NO_2$ —C(═O)H, or —$CH_2OCH_3$, or a pharmaceutically acceptable salt thereof.

3. The method of claim 1 wherein A is 2-quinolinyl.
4. The method of claim 2 wherein A is 2-quinolinyl.
5. The method of claim 1 wherein A is 3-quinolinyl.
6. The method of claim 2 wherein A is 3-quinolinyl.
7. The method of claim 1 wherein A is 6-quinolinyl.
8. The method of claim 2 wherein A is 6-quinolinyl.
9. The method of claim 1 wherein $R^1$ and $R^2$ are hydrogen, and $R^3$ is halogen, $C_1$–$C_6$ alkyl, or hydroxymethyl.
10. The method of claim 2 wherein $R^1$ and $R^2$ are hydrogen, and $R^3$ is halogen, $C_1$–$C_6$ alkyl, or hydroxymethyl.

11. The method of claim 1 wherein $R^1$ is hydrogen, and $R^2$ and $R^3$ are independently halogen, hydroxymethyl, —$CF_3$, $C_1$–$C_6$alkyl, $C_1$–$C_6$ alkoxy, —CN, —C(=O)H, —$CH_2OCH_3$.

12. The method of claim 2 wherein $R^1$ is hydrogen, and $R^2$ and $R^3$ are independently halogen, hydroxymethyl, —$CF_3$, $C_1$–$C_6$alkyl, $C_1$–$C_6$ alkoxy, —CN, —C(=O)H, —$CH_2OCH_3$.

13. The method of claim 1 wherein A is 2-quinolinyl, $R^1$ and $R^2$ are hydrogen, and $R^3$ is halogen, $C_1$–$C_6$ alkyl, or hydroxymethyl.

14. The method of claim 2 wherein A is 2-quinolinyl, $R^1$ and $R^2$ are hydrogen, and $R^3$ is halogen, $C_1$–$C_6$ alkyl, or hydroxymethyl.

15. The method of claim 1 wherein A is 2-quinolinyl, $R^1$ is hydrogen, and $R^2$ and $R^3$ are independently halogen, hydroxymethyl, —$CF_3$, $C_1$–$C_6$ alkyl, $C_1$–$C_6$alkoxy, —CN, —C(=O)H or —$CH_2OCH_3$.

16. The method of claim 2 wherein A is 2-quinolinyl, $R^1$ is hydrogen, and $R^2$ and $R^3$ are independently halogen, hydroxymethyl, —$CF_3$, $C_1$–$C_6$ alkyl, $C_1$–$C_6$alkoxy, —CN, —C(=O)H, or —$CH_2OCH_3$.

17. The method of claim 1 wherein the compound of Formula I is:
2-(4-p-tolyl-piperazin-1-ylmethyl)-quinoline;
2-[4-(3-chloro-phenyl)piperazin-1-ylmethyl]-quinoline;
[2-chloro-4-(4-quinolin-2-ylmethyl-piperazin-1-yl)phenyl]-methanol;
2-[4-(3,4-dimethyl-phenyl)-piperazin-1-ylmethyl]-quinoline;
2-[4-(3-chloro-4-methoxymethyl-phenyl)-piperazin-1-ylmethyl]-quinoline;
[2-bromo-4-(4-quinolin-2-ylmethyl-piperazin-1-yl)-phenyl]-methanol;
2-[4-(3-chloro-4-methyl-phenyl)piperazin-1-ylmethyl]-quinoline;
2-[4-(3-bromo-phenyl)-piperazin-1-ylmethyl]-quinoline;
2-[4-(3-propyl-phenyl)-piperazin-1-ylmethyl]-quinoline;
2-[4-(2,3-dichloro-phenyl)piperazin-1-ylmethyl]-quinoline;
2-[4-(3,4-dichloro-phenyl)piperazin-1-ylmethyl]-quinoline;
[2-fluoro-4-(4-quinolin-2-ylmethyl-piperazin-1-yl)-phenyl]-methanol;
2-chloro-4-(4-quinolin-2-ylmethyl-piperazin-1-yl)-benzaldehyde;
2-chloro-4-(4-quinolin-2-ylmethyl-piperazin-1-yl)-benzonitrile;
2-[4-(4-methoxy-phenyl)piperazin-1-ylmethyl]-quinoline;
2-[4-(3,5-dichloro-phenyl)piperazin-1-ylmethyl]-quinoline;
2-[4-(4-chloro-3-trifluoromethyl-phenyl)-piperazin-1-ylmethyl]-quinoline;
2-(4-m-tolyl-piperazine-1-ylmethyl)-quinoline;
[4-(4-quinolin-2-yl-methylpiperazin-1-yl)-phenyl]-methanol;
[2-fluoro-4-(4-quinolin-3-ylmethyl-piperazin-1-yl)-phenyl]-methanol;
[2-bromo-4-(4-quinolin-3-ylmethyl-piperazin-1-yl)-phenyl]-methanol;
3-(4-phenyl-piperazin-1-ylmethyl)-quinoline;
3-(4-p-tolyl-piperazin-1-ylmethyl)-quinoline;
6-(4-phenyl-piperazin-1-ylmethyl)-quinoline; or
3-[4-(2-fluoro-phenyl)piperazin-1-ylmethyl]-quinoline.

18. The method of claim 2 wherein the compound of Formula I is:
2-(4-p-tolyl-piperazin-1-ylmethyl)-quinoline;
2-[4-(3-chloro-phenyl)piperazin-1-ylmethyl]-quinoline;
[2-chloro-4-(4-quinolin-2-ylmethyl-piperazin-1-yl)phenyl]-methanol;
2-[4-(3,4-dimethyl-phenyl)-piperazin-1-ylmethyl]-quinoline;
2-[4-(3-chloro-4-methoxymethyl-phenyl)-piperazin-1-ylmethyl]-quinoline;
[2-bromo-4-(4-quinolin-2-ylmethyl-piperazin-1-yl)-phenyl]-methanol;
2-[4-(3-chloro-4-methyl-phenyl)piperazin-1-ylmethyl]-quinoline;
2-[4-(3-bromo-phenyl)-piperazin-1-ylmethyl]-quinoline;
2-[4-(3-propyl-phenyl)-piperazin-1-ylmethyl]-quinoline;
2-[4-(2,3-dichloro-phenyl)piperazin-1-ylmethyl]-quinoline;
2-[4-(3,4-dichloro-phenyl)piperazin-1-ylmethyl]-quinoline;
[2-fluoro-4-(4-quinolin-2-ylmethyl-piperazin-1-yl)-phenyl]-methanol;
2-chloro-4-(4-quinolin-2-ylmethyl-piperazin-1-yl)-benzaldehyde;
2-chloro-4-(4-quinolin-2-ylmethyl-piperazin-1-yl)-benzonitrile;
2-[4-(4-methoxy-phenyl)piperazin-1-ylmethyl]-quinoline;
2-[4-(3,5-dichloro-phenyl)piperazin-1-ylmethyl]-quinoline;
2-[4-(4-chloro-3-trifluoromethyl-phenyl)-piperazin-1-ylmethyl]-quinoline;
2-(4-m-tolyl-piperazine-1-ylmethyl)-quinoline;
[4-(4-quinolin-2-yl-methylpiperazin-1-yl)-phenyl]-methanol;
[2-fluoro-4-(4-quinolin-3-ylmethyl-piperazin-1-yl)-phenyl]-methanol;
[2-bromo-4-(4-quinolin-3-ylmethyl-piperazin-1-yl)-phenyl]-methanol;
3-(4-phenyl-piperazin-1-ylmethyl)-quinoline;
3-(4-p-tolyl-piperazin-1-ylmethyl)-quinoline;
6-(4-phenyl-piperazin-1-ylmethyl)-quinoline; or
3-[4-(2-fluoro-phenyl)piperazin-1-ylmethyl]-quinoline.

* * * * *

UNITED STATES PATENT AND TRADEMARK OFFICE
CERTIFICATE OF CORRECTION

PATENT NO. : 5,945,421
DATED : Aug. 31, 1999
INVENTOR(S) : Belliotti et al.

It is certified that error appears in the above-identified patent and that said Letters Patent is hereby corrected as shown below:

Column 12, line 36, "—$NO_2$" should read -- —$NO_2$, --.

Column 12, line 55, "—$NO_2$" should read -- —$NO_2$, --.

Signed and Sealed this

Ninth Day of May, 2000

Attest:

Attesting Officer

Q. TODD DICKINSON

Director of Patents and Trademarks